United States Patent [19]

Franetzki et al.

[11] Patent Number: 4,559,037
[45] Date of Patent: * Dec. 17, 1985

[54] DEVICE FOR THE PRE-PROGRAMMABLE INFUSION OF LIQUIDS

[75] Inventors: Manfred Franetzki, Uttenreuth; Klaus Gagneur, Bubenreuth; Karl Prestele, Erlangen, all of Fed. Rep. of Germany

[73] Assignee: Siemens Aktiengesellschaft, Berlin & Munich, Fed. Rep. of Germany

[ * ] Notice: The portion of the term of this patent subsequent to Aug. 11, 1998 has been disclaimed.

[21] Appl. No.: 572,417

[22] Filed: Jan. 20, 1984

Related U.S. Application Data

[63] Continuation of Ser. No. 238,137, Feb. 25, 1981, abandoned, Continuation-in-part of Ser. No. 969,189, Dec. 13, 1978, Pat. No. 4,282,872.

[51] Int. Cl.$^4$ ............................................. A61M 37/00
[52] U.S. Cl. ....................... 604/151; 604/891
[58] Field of Search ..................... 604/65–67, 604/19–21, 890, 891, 30–31, 27–28, 49–50, 131, 604/151, 153–154; 128/DIG. 12, DIG. 13

[56] References Cited

U.S. PATENT DOCUMENTS 3,894,538  7/1975  Richter ............................... 604/891
3,923,060  12/1975  Ellinwood, Jr. ..................... 604/891
4,077,405  3/1978  Haerten et al. .............. 128/DIG. 13
4,140,122  2/1979  Kuhl et al. .......................... 604/891
4,146,029  3/1979  Ellinwood, Jr. ..................... 604/891

OTHER PUBLICATIONS

Martin, P. et al., "Normalization of Insulin Delivery to Diabetics by Pulsed Insulin Infusion" *IEE Transactions on Biomedical Engineering,* BME-24, No. 2, Mar. 1977, pp. 116–121.

Primary Examiner—William E. Kamm
Attorney, Agent, or Firm—Hill, Van Santen, Steadman & Simpson

[57] ABSTRACT

Particularly for diabetes therapy, it is desirable to continuously infuse insulin in different rates into the body of the patient, because the insulin requirements of the diabetic are subject to great fluctuations. Therefore, a control device serves as the program transmitter for a microdosing unit. The control device for the microdosing unit has memory means for a prescribable control program allocated to it, whereby the control program can be called up directly by the patient at the control device. The program sequence of the infusion is started only by means of the dialing-up of a plurality of insulin units to be delivered into the body or of relevant food values taken in by the patient with a meal and of a starting time ($T_1$, $T_2$). In addition, specific base rates of the infusion can be selected by the patient. With the invention device, diabetes patients can call up the necessary insulin administration according to short programs at meals.

30 Claims, 10 Drawing Figures

DEVICE FOR THE PRE-PROGRAMMABLE INFUSION OF LIQUIDS

CROSS REFERENCE TO RELATED APPLICATIONS

The present application is a continuation of our application for patent U.S. Ser. No. 238,137 filed Feb. 25, 1981, now abandoned, which in turn is a continuation-in-part of our application for patent U.S. Ser. No. 969,189 filed Dec. 13, 1978, now U.S. Pat. No. 4,282,872 issued Aug. 11, 1981. The present application relates to an improvement with respect to our copending application for patent U.S. Ser. No. 969,200 filed Dec. 13, 1978, now U.S. Pat. No, 4,270,532 issued June 2, 1981, and this U.S. Pat. 4,270,532 is incorporated herein by reference by way of background.

BACKGROUND OF THE INVENTION

The invention relates to a device for the preprogrammable infusion of liquids into the human or animal body, particularly for the administration of insulin in diabetes therapy, comprising a microdosing unit for the liquid as well as a control device as a program transmitter for the microdosing unit. Thereby, the microdosing unit for the liquid can be implanted in the body together with or separate from the control device or can also be carried externally on the body surface.

In diabetes therapy, it is desirable to continuously infuse insulin to the body of the patient in varying installments, because the need of the diabetic for insulin during the day is subject to great fluctuations, determined, for example, by the rhythm of the meals. It has been shown that—as long as no infusion devices that regulate themselves automatically by means of glucose sensors are available—the delivery of insulin should best ensue according to a daily profile that can be individually adjusted and preprogrammed for the patient. Thereby, it is possible, in a device of the type initially cited, to allocate memory means for a prescribable control program at least to the control device for the microdosing unit, whereby the control program is pre-programmable in discrete time steps corresponding to the 24-hour daily sequence at an external programming device and the control device is electrically connected to the programming device or a program carrier, respectively, solely for the transfer of the pre-programmed control program. Such a device has the advantage that the pre-programming of the daily profile can be carried out in a simple and clear manner by the physician; for example, such devices can then be used when, during a longer examining period when the patient is in the hospital under the supervision of the physician, an optimum daily infusion profile for a subsequent infusion installation to be completely implanted or also for a later, standard injection therapy is to be ascertained. However, in this case the patient in general has no direct access for alterning the pre-programmed dosage and is, therefore, bound to a relatively regular daily course with the ingestion of his meals predetermined both in terms of time and amount.

In certain cases of diabetes, however, binding the patient to a regular daily course is not absolutely necessary. Based on the constituion of the patient, it can be possible that the patient can pursue a relatively irregular daily course insofar as the necessary insulin doses are administered to him at the necessary times at meals. In such a case, therefore, the constraint of the patient to the daily profile of the pre-programmed insulin administration is unnecessary and can even become a burden for the patient.

INCORPORATION BY REFERENCE

Background concerning the present invention is found in an article entitled "Development of Program-controlled Portable Insulin Delivery Devices" by K. Prestele and M. Franketzki, two of the inventors herein, and H. Kresse, published in Diabetes Care, Vol. 3, No. 2, March-April 1980, pages 362-368, and this article is incorporated herein by reference.

So far as the article pertains to a demand type delivery system, the decisive features are as follows:

(1) In the control apparatus specific short-term programs with prescribed infusion profiles are stored.

(2.1) Only the entire infusion (International insulin units) to be administered is selected during or after a meal by the patient.

(2.2) Alternatively thereto, the quantity of carbohydrates absorbed with the meal (carbohydrate content of the meal) can be indicated.

(3) The infusion program is started by the patient with input of the dose and runs to completion in conformity with the prescribed infusion profile.

In the article, a demand type delivery system is apparent from the third and fourth figures.

SUMMARY OF THE INVENTION

Certain material relating to figures four, five A and five B of an application for patent of two of the present inventors, namely Franetzki and Prestele U.S. Ser. No. 150,180 filed May 15, 1980, which was originally incorporated herein by reference, has now been physically incorporated herein as FIGS. 4, 5A and 5B; the respective related description, for illustrating implementations within the scope of the broad teachings of the present invention, being found herein under the heading "DISCLOSURE FROM RELATED APPLICATION".

The object of the invention is therefore to create a further device of the type initially cited with which, on the one hand, a pre-programmed infusion is made possible, but which, on the other hand, leaves the patient a certain freedom in the time of ingesting meals. The programmed sequence of the infusion should indeed correspond with the actual infusion requirement as far as possible, but be able to be temporally influenced by the patient.

The object is inventively achieved in that the control device for the microdosing unit has memory means for a prescribable control program allocated to it, which control program can be directly called up by the patient at the control device, and in that the programmed sequence of the infusion is started only through the dialing-up of a plurality of the insulin units to be emitted into the body or of the carbohydrate units ("bread units") taken in by the patient with the meal, respectively, and a starting time.

With the invention, therefore, a possibility is created to combine the advantages of devices for pre-programmable infusion with the possibility of a delivery of infusion liquid that is variable in terms of time and amount. At a meal or at the end of a meal, the patient only selects an equivalent amount of insulin units corresponding to the "bread units" taken in at the meal on the control device which he carries, whereby in so doing a pre-programmed control program covering a number of hours is called up from a program transmitter.

In an advantageous embodiment of the invention, on the one hand a constant base rate is adjusted at the control device, to which the additional insulin administrations are superimposed as a rectangular pulse-rate versus time function as needed at a meal. In this case, either the delivery time or the pulse rate is predetermined as constant, so that the programmed sequence ensues only by means of the selection of the other parameter which determines the area encompassed by the rectangular function i.e. the insulin amount dispensed over the total delivery time. As an alternative, by means of prescribing rectangle functions with changeable amplitude and width upon the dialing-up of an n-fold insulin amount, in any given case the ratio of infusion time and rate can also be changed.

In a further advantageous embodiment of the invention, the control program of the infusion rate essentially corresponds to a triangular pulse rate versus time function, for example, right-angled triangle, whereby the infusion rate quickly rises from a base value to the highest value and subsequently decreases again from the highest value to the base value with a predetermined functional dependency. Thereby, the rate of decrease is preferably linear as a function of the predetermined initial increase. But the decrease as a function of time can also be exponential in the manner of an e-function. The infusion rate output can, of course, also be constructed more complexly in terms of its variation with time and resultant total area and be matched to the actual insulin delivery of a natural pancreas, whereby upon erection of a profile with nonlinear functional dependencies a computer (microprocessor) is to be provided for matching the dialed-up infusion amount to the delivery profile.

The infusion device created with the invention preferably consists of two individual devices. Thereby, the microdosing unit can be optionally designed as an implant with transcutaneous signal transmission from the control device to be carried on the exterior of the body or as a device to be arranged on the exterior of the body along with the control device. In the latter case, a direct line connection for signal transmission between the two devices is then possible. Further advantages and details of the invention derive from the following description of exemplary embodiments on the basis of the accompanying sheets of drawings in conjunction with the claims; and other objects, features and advantages will be apparent from this detailed disclosure and from the appended claims.

BRIEF DESCRIPTION OF THE DRAWINGS

FIG. 3 comprising

DETAILED DESCRIPTION

Figure 1:
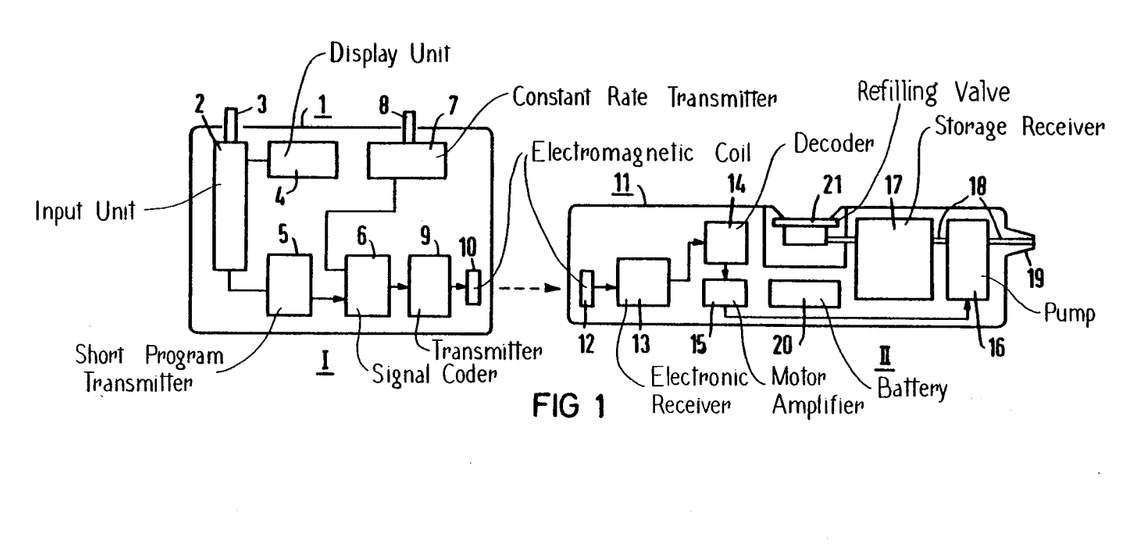
FIG. 1 is a basic representation of a control device and a microdosing unit with block diagrams therein to show the individual functional units.

In FIG. 1, a control device is indicated at I and a microdosing unit at II. The control device I consists of a device housing 1 about the size of a pocket calculator, which contains the electronic component parts and whose operation is selectable from the outside by means of a plurality of operating elements. In an input unit 2, the number of insulin units to be delivered is selected via an actuating member 3, said number of insulin units being visible on the device housing 1 at a display unit 4. A short program transmitter 5 is controlled by the input unit 2, in which short program transmitter program sequences between about 0.5 and 3 hours for the infusion rate are stored, which are started by means of being fetched with the input of the insulin units to be delivered. As the program transmitter 5, for example, digital semiconductor memories, so-called RAM's, are used which are programmable for program sequences as desired. The program transmitter 5 controls a signal coder 6 which appropriately prepares the selected program for signal transmission. The signal coder 6 is further controllable by a constant rate transmitter 7 with actuation member 8. The coded signals are delivered from the signal coder 6 to a transmitter 9 with which an electromagnetic coil 10 is connected for purposes of remote control.

In the exemplary embodiment, the control signals are to be transmitted wirelessly, and, indeed, inductively. Instead of an inductive signal transmission, of course, other electromagnetic signal transmission processes for example infrared or ultrasonic signal transmission processes are also possible. As an alternative to that, in an extracorporeal arrangement of the microdosing unit, the control device can also be coupled to the microdosing unit via a direct electric line connection.

The housing of the microdosing unit II is indicated at 11. Analogous to the control device I, it contains a receiver coil 12 with an electronic receiver 13 and decoder 14 connected on the output side. A motor driving amplifier 15 is controlled via the decoder 14, with which motor driving amplifier the drive motor of a mechanical pump 16 is driven. By means of the pump 16, the liquid insulin is conveyed out of a storage reservoir 17 to a catheter connection 19 on the device housing 11 via a connection line 18. Further, the housing 11 of the microdosing unit II also contains a battery 20 as an energy source for the pump drive the housing also contains a refilling valve 21, via which insulin can be refilled into the storage reservoir 17 by means of an injection through a membrane that automatically closes itself—transcutaneously in the case of an implanted microdosing unit, if necessary.

Figure 2:
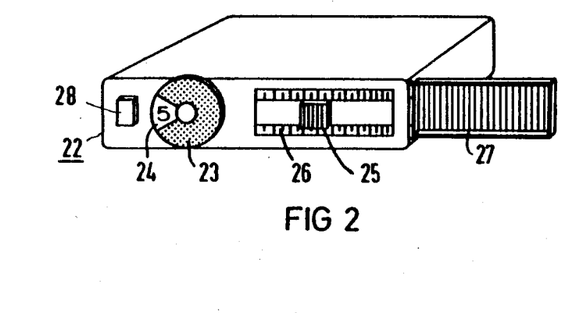
FIG. 2 is an exterior view of a control device in perspective representation.

In FIG. 2, the housing of a control device is indicated at 22. A rotary switch 23 is located on its side face, with which discrete infusion amounts are selected in insulin units (for example, in steps from 1 through 10 IE) represented by indicia on a selector dial 24, which infusion amounts are input into the program transmitter 5. A sliding switch 25 is arranged next to it, with which constant base rates of the insulin delivery (for example adjustable between 0.4 and 2 IE/h) can be adjusted on a scale 26. Since, in general, the base rate is only prescribed once and is then not to be changed for a relatively long time, the scale 26 is covered by a flap 27 in the operating state of the control device.

In the pulse diagrams according to FIG. 3, the flow rate of the microdosing unit II is illustrated for various short programs as a function of time. In each case, the straight lines 30 parallel to the abscissa indicate that a constant base rate for the delivery of insulin units is adjusted, namely 1 IE/h. In the pulse diagram of FIG. 3a, the delivery rate at the selecting time $T_1$ rises from 1 IE/h to 3 IE/h and after an hour decreases to the initial value. At the selection time $T_2$, the delivery rate rises to an infusion rate of 7 IE/h and after an hour decreases to the initial value. The rectangles 31 or 32, respectively, superimposed on the constant delivery rate correspond to a total insulin delivery of 2 IE or 6 IE, respectively. For such a delivery, thus, only the delivery time of one hour is stored in the program transmitter 5. After his meal (at time $T_1$ or $T_2$), the patient then need only select the required insulin units on switch 23, whereupon the delivery rate changes for the prescribed time span.

Figure 3A:
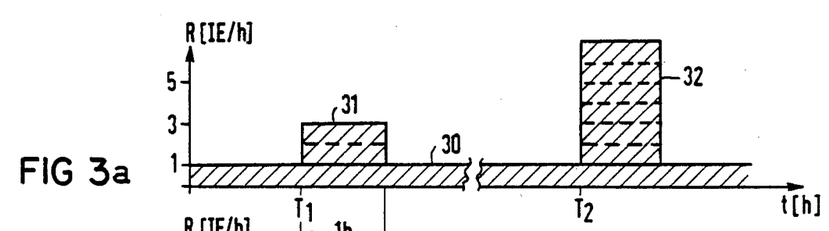
FIGS. 3a-3e shows various pulse diagrams for possible program-wise predetermined infusion rates of the insulin delivery.
Figure 3B:
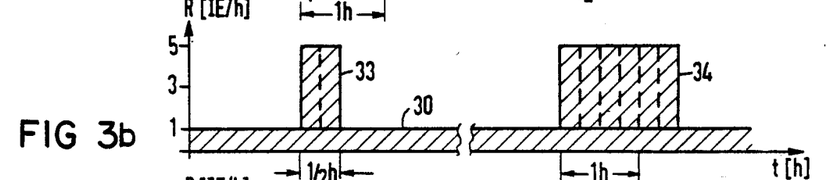

In the pulse diagram of FIG. 3b, on the other hand, the delivery rate is given as a constant. By means of selecting the insulin units on switch 23, the time span of the insulin delivery, which is changeable from, for example, 0.5 through 3 hours, is determined by the program transmitter. In this case, the rectangles 33 or 34, respectively, again indicate superimposed values of 2 IE or 6 IE, respectively.

Figure 3C:
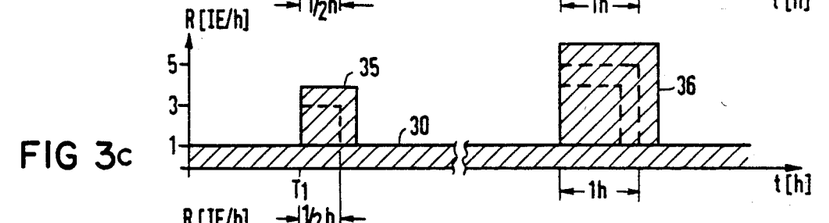

In the pulse diagram of FIG. 3c, a primary rectangle with the edge length and height, t=0.5 h and I=2 IE/h is constructed. Such a rectangle is storable in program transmitter 5 as a square function with corresponding scaling. Upon doubling of the area of such a scaled primary square function, the edge lengths and heights in any given case change in the ratio $\sqrt{2}:1$. Accordingly, the squares 35 or 36, respectively, again indicate 2 IE or 6 IE, respectively. A multiplication of the insulin amount by the factor n, accordingly, produces a change of the delivery time and delivery rate by the factor $\sqrt{n}$.

Figure 3D:
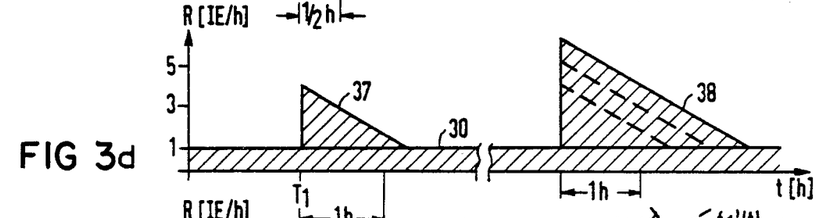
Figure 3E:
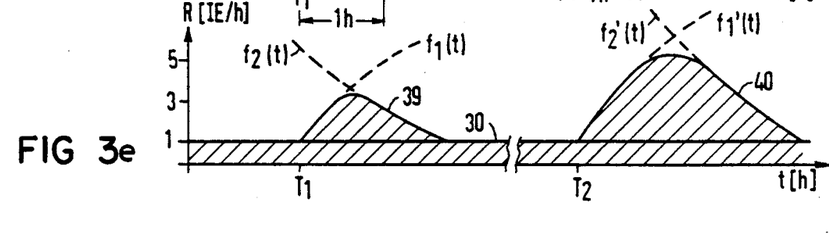

In the pulse diagram of FIG. 3d, at time $T_1$ the delivery rate is increased from the base value 1 IE/h to a value of 4 IE/h and thereafter decreases linearly with a prescribed slope to the initial value. At time $T_2$, the delivery rate is increased to a value of 6 IE/h, from where it likewise returns to the initial value with the same prescribed slope. In this case, thus, congruent triangles are set up to represent the functions in each case on the constant base rate, whereby the triangle 37 again corresponds to 2 IE and the triangle 38 to 6 IE. Accordingly, the delivery rates and times change in a tripled delivery by increasing each of the triangle sides representing delivery rate and time in the ratio $\sqrt{3}$, whereby the slope of the hypotenuse of the triangle is stored in the program transmitter. Instead of the straight lines, a e-function can be provided for the decrease of the infusion rate from the highest value to the base value. The insulin delivery in a triangular form has the advantage, particularly, that the transition from the increased delivery rate to the normal base rate does not occur abruptly, but rather gradually in a time-continuous manner.

If one analyzes the actual insulin requirements in the case of a meal and subsequent digestion in detail, then, corresponding to the insulin delivery of a natural pancreas, one first obtains a quick increase to a highest value with a superimposed peak and a subsequent slow decrease to the initial value in the manner of e-functions. This actual need, however, can only be matched by means of several exponential functions, whereby the encompassed area is then naturally more complex to realize. Such a course of the delivery rate is illustrated in a simplified manner in the pulse diagram of FIG. 3e with two adapted functions. The delivery rates are determined by means of the exponential functions $f_i^k(t)$, whereby the free parameters are adaptable as desired. In such a case, however, the program transmitter must have a computer, for example, a microprocessor, allocated to it, which adapts the infusion amount selected by the patient, i.e. a given total area, to the area actually desired with prescribed contours corresponding to the functional dependency stored in the program transmitter.

It has turned out that in specific individual cases -for example after a meal that is difficult to digest - it can be necessary to vary the delivery time in deviation from the pre-programmed short program. In the pulse diagram according to FIG. 3d, this means, for example, that the slope of the straight lines is changeable. To this end, a further step-switch 28 for time retardation is provided on the control device according to FIG. 2, with which the patient can adjust a time scale of the program to correspond with the digestibility and resorption of an ingested meal.

In the device according to German Offenlegungsschrift No. 2,451,424, the daily sequence of the infusion is pre-programmable on the programming panel of a control unit. By means of such a pre-programming, the infusion device delivers a constant base rate and, upon need, a peak rate superimposed upon this base rate, for example, according to FIGS. 2 or 3 of the U.S. Pat. No. 4,077,405. In such a control, the patient is forced to arrange his day with the ingestion of meals, etc., according to the pre-programmed daily program.

The invention eliminates these disadvantages in that the patient can call up short programs at any desired times corresponding to the requirements existing at any given time. Thereby, specifically for diabetes therapy, the patient need only select the amount of the required insulin units (IE) or the bread units (BE) taken in with a meal, respectively, in order to let the infusion proceed according to the desired program. The abbreviation "IE" stands for "Internationale Einheit" in in the German language, or international unit in English. (The abbreviation BE is a recognized abbreviation in German medical practice, referring to a unit for calculating the amount of carbohydrate for the diet, e.g. in the case of diabetes.)

It will be apparent that many modifications and variations may be effected without departing from the scope of the novel concepts and teachings of the present invention.

Disclosure From Related Application

Figure 4:
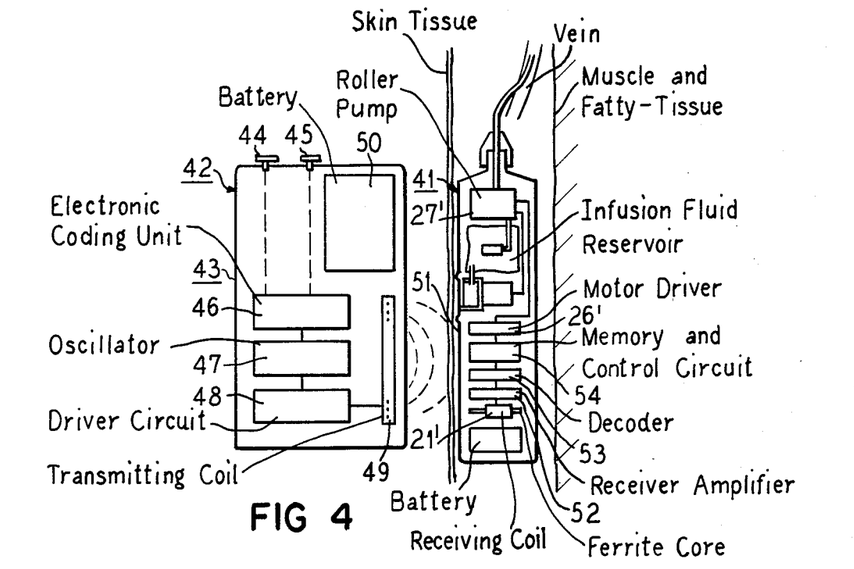
FIG. 4 illustrates the construction of the control apparatus in the case of an embodiment incorporated herein from pending application for patent U.S. Ser. No. 150,180 filed May 15, 1980.

The change-over control device 42 in FIG. 4 has, on its device housing 43, as an input unit, only the selector elements 44 and 45 for the selection of the basal rate and callup dose, which elements directly influence (or act upon) the program transmitter means including an electronic coding unit 46. An oscillator 47, a driver 48, and a transmitting coil 49 are, in turn, connected at the output side of the coding unit 46. In the housing 43, a battery 50 as the energy supply is furthermore arranged.

The infusion device 41 has an implantable housing 51. The device 41, in addition to the receiving coil 21', and units 26' and 27', has a receiving circuit comprising components 52, 53 and 54. From the receiving coil 21', a receiving amplifier 52 with an output-connected decoder 53 is activated. A memory and control curcuit 54 is output-connected with the decoder 53, which circuit shall be described in detail in connection with FIGS. 5A and 5B. From this specifically designed control and memory circuit 54, a motor driver 26' for infusion pump 27' is activated in the above-described fashion.

In this exemplary embodiment, the signal transmission proceeds only over a minimal distance of a maximum of one-tenth meter (0.1 m), since the receiving circuit of the implanted infusion device 42 is to be changed-over only in the case of directly adjacent application of the control device 42.

Figure 5A:
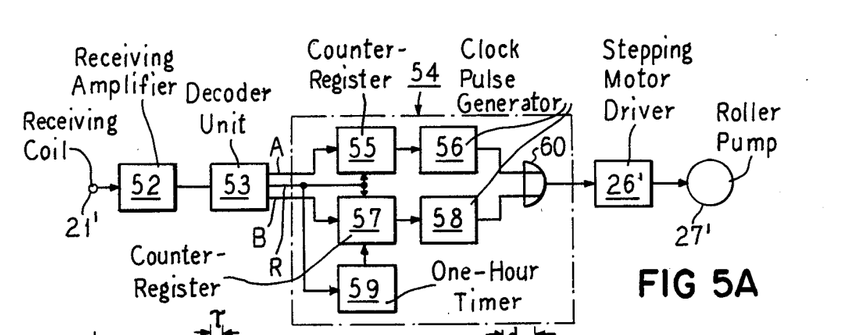
FIGS. 5A and 5B illustrate the construction and operation of the receiving circuitry according to FIG. 4 for the purpose of changing-over of the basal rate and the call-up program.
Figure 5B:
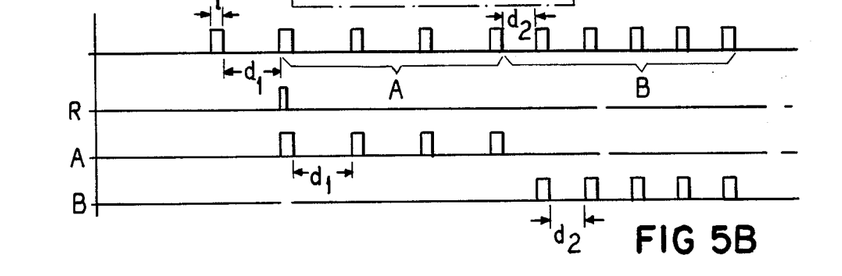

In FIGS. 5A and 5B, reference numerals 21', 26', 27', 52 and 53, denote units known from FIG. 4. The memory and control circuit 54 essentially consists of two counters 55 and 57 with output-connected clock pulse generators 56, and 58, respectively, as well as one-hour timer 59, and a logic-coupling element 60. The decoder unit 53 has three outputs A, B and R. From the output A, a first counter 55, as the basal rate memory is activated together with clock pulse generator 56; from the second output B, a second counter 57 as the call-up rate memory for superimposing an additional dose, is activated together with clock pulse generator 58. The signals of the two clock pulse generators 56 and 58 are logic-linked via a gate 60, so that there results, at this output, a summation of the two clock pulse sequences in the form of a superposition of basal rate and additional call-up rate. The stepping motor drive 26' is activated by the resultant clock pulse signal from gate 60. Prior to re-programming, both counters 55 and 57 are reset to zero, respectively, from the signal-output R of the decoder 53. Simultaneously, the signal R triggers the timer 59 which, after expiration of a prescribed time, for example one hour (1 h), resets counter 57 to zero. The additional call-up rate is thus switched off after being active for a relatively short time interval which is determined by timer 59, for example a time interval of one hour.

Thus, with the external control device, the receiving circuit in the infusion device 41 can be changed-over at any time. This is illustrated in the pulse diagram of FIG. 5B: the decoder 53 separates pulse salvos with different pulse intervals $d_1$ and $d_2$. The decoder 53 recognizes a first double pulse signal with pulse interval $d_1$ as the key signal and supplies a reset pulse R for the counters 55 and 57, and timer 59. The previously stored information in counters 55 and 57 is thus cancelled. The first pulse salvo (sequence A, FIG. 5B) with pulse interval $d_1$ then loads the first memory 55 via line A, FIG. 5A, to the value for the basal rate determined by the position of selector 44 on the control device 42 (e.g. a count of four); the second pulse salvo (sequence B, FIG. 5B) with pulse interval $d_2$ loads the second memory i.e. counter register 57 via line B, FIG. 5A, to the value for the additional dose as determined by the position of the selector 45 on the control device 42 (e.g. a count of five). Thus, after change-over control, a newly adjusted basal rate (e.g. .4 International insulin units per hour) is delivered by the infusion device 41, on which basal rate, a correspondingly adjusted call-up dose (e.g. five International insulin units) is set-up to provide a superimposed dose whose duration is controlled by timer 59. Subsequent to delivery (or dispensing) of this call-up dose (providing for example a total rate of 5.4 IE for one hour), the transport again proceeds with the adjusted basal rate (e.g. .4 International insulin units per hour) as determined by the count value in counter-regis-ter memory 55, the counter-register 57 being reset to a count value of zero by the timer 59 at the completion of its timing cycle.

In FIGS. 4, 5A and 5B, actuation of a momentary switch such as 28, FIG. 2, may be used to initiate the transmission of a signal sequence such as represented in FIG. 5B herein. Thus after setting the selectors 44, 45, FIG. 4, the user would actuate the momentary start switch to actually transmit the selected settings to the register counters 55 and 57, FIG. 5A (after resetting components 55, 57, 59, FIG. 5A), so that the desired new infusion schedule would be actually carried out by components 55-60, and 26', 27', FIG. 5A.

In the corresponding European proceedings, the following main claim has now been allowed:

Device for the preprogrammable infusion of liquids into human or animal bodies, particular to administering insulin in diabetes therapy, consisting of a micro-dose unit for the liquid and a control device which is connected thereto, has a programmer for the micro-dose unit and is assigned storage means for a predeterminable control programme, characterized in that the control device (1) possesses an input unit (2) with which the patient can directly enter, in accordance with carbohydrate content (BU) absorbed by the patient at a meal time the number of insulin units (IU) to be dispensed into the body with a timing in conformity with the control programme, and that the selection process serves to start the programme sequence of the infusion.

For a control of basal infusion rate, a basal counter register such as 55, FIG. 5A, can be loaded according to the setting of the basal rate selector each time a momentary start switch is actuated. Such counter register would then replace the BCD decoder (77) of the third figure of U.S. Pat. No. 4,270,532 in controlling a basal binary rate multiplier.

A short time infusion rate can be introduced by using a selector to control loading of a one-hour counter register such as 57, FIG. 5A, the momentary start switch actuation serving to initiate a one-hour timing cycle of a timer such as 59, FIG. 5A, which then resets the one-hour counter register to zero after such one hour time interval.

During the time the one-hour counter register has a non-zero count therein, it controls a one-hour binary rate multiplier circuit to superimpose pulses on the basal rate pulses via a buffer such as indicated at 60 in FIG. 5A.

The implementation of other embodiments will be apparent from the foregoing. For example coding unit 46 will send pulse sequences as in FIG. 5B to load binary counter registers 55 and 57, FIG. 5A, which can then control binary rate multipliers including the clock pulse gneerators 56 and 58, to supply basal and superimposed one-hour infusion pulses via mixer 60.

DISCUSSION OF CLAIM TERMINOLOGY

From the standpoint of claim terminology the means operated by input units 45 and 46, FIG. 4, including components 46-49 will be broadly designated program transmitter means.

Also from the standpoint of claim terminology, respectively selectable infusion schedules such as indicated at 31 and 32 in FIG. 3a, or at 33 and 34, FIG. 3b, may be regarded as manually selectable pre-established infusion programs having respective insulin infusion profiles as a function of time and with respective limited time durations suitable to the ingestion of an individual meal.

As previously explained in reference to selector 25 and scale 26, FIG. 2, the maximum selectable basal infusion rate may be two insulin units per hour, so that the call-up dose selector 23, FIG. 2, has many discrete selection positions corresponding to rates of infusion higher than two insulin units per hour. For example, FIG. 3a shows possible selection of a rate of two units per hour at 31, and indicates by dash lines at 32 possible selections of three, four, five or six units per hour (superimposed on a basal rate of one unit per hour), specifically showing at 32 a call-up rate of six insulin units per hour added to a basal rate of one unit per hour for a total rate of seven units per hour during a one hour limited time interval. In the description of FIG. 3a, it is stated that program transmitter 5 may operate with switch 23, so that discrete selectable call-up delivery rates between one insulin unit per hour and ten insulin units per hour are disclosed herein.

As indicated in FIG. 3a, for example, where the basal infusion rate is constant at one unit per hour over a relatively long basal infusion time interval, the call-up programs manually selected for each individual meal may have an infusion rate of two units per hour or five units per hour. As previously explained in reference to rotary switch 23, FIG. 2, descrete infusion amounts may be selected in insulin units, for example in steps from one through ten International insulin units, and selections may be represented by indicia on a selector dial 24, FIG. 2. Thus FIG. 3a, along with FIG. 2 and its description show that the selection range of the input unit 23 may provide a range of amounts of insulin from a low insulin amount of one unit (over a limited time duration of one hour) to a high insulin amount of five units, FIG. 2, or six units, (as shown at 32, FIG. 3a, or at 34, FIG. 3b). Thus the high call-up insulin amount is many times, e.g. five or six times the low call-up insulin amount.

The present subject matter is particularly concerned with a glucose sensorless device where the insulin infusion profile for each individual meal is essentially determined by the manual selection of a single number. The input to be selected for each meal is essentially the single parameter, e.g. amount of insulin to be infused, the apparatus itself automatically determining an insulin infusion profile and a limited call-up infusion time interval suitable to an individual meal and to the selected insulin dosage. In this sense infusion is preprogrammable even though call-up doses are to be manually selected at each individual meal.

From the standpoint of the embodiment of FIGS. 4, 5A and 5B, the control means may be regarded as storing a selected control program as selected by input unit 45 in storage means 57, FIG. 5A, the components 57, 58 and 59 being structured to generate an insulin infusion profile in accordance with the selected control program.

For the embodiment of the fourth figure at page 364 of the incorporated article from *Diabetes Care*, March-April 1980, the switch $S_a$ operated by the input unit is a storage means for the selected control program, and the program transmitter includes the one hour gate (1h - gate) and motor clock components.

We claim as our invention:

1. Apparatus for the infusion of insulin into a patient's body in diabetes therapy, comprising a microdosing unit for supplying said insulin to the patient's body, control means selectively controlling said microdosing unit to supply respective different amounts of insulin with respective corresponding predetermined insulin infusion profiles as a function of time and with a limited time duration suitable to an individual meal, said control means selectively generating respective control signals which control the supply of the respective different amounts of insulin by the microdosing unit with the respective corresponding predetermined insulin infusion profiles, said control means having an input unit manually operable directly by the patient for entering, in accordance with the carbohydrate content of a meal, a selected input signal corresponding to a respective required amount of insulin to be delivered into the body of the patient, said input unit controlling said control means to supply a respective control signal according to the selected input signal, to said microdosing unit, such that said microdosing unit delivers the corresponding required amount of insulin into the patient's body with the corresponding predetermined infusion profile as a function of time, said input unit having a selection range of input signals corresponding to a range of amounts of insulin such that the amount of insulin selectable by said input unit is individually adaptable to each of the patient's meals.

2. Apparatus according to claim 1, with said microdosing unit supplying a constant basal rate of insulin greater than zero during a basal infusion time interval which is greater than the limited time duration of each predetermined insulin infusion profile.

3. Apparatus according to claim 2, with each predetermined insulin infusion profile having a limited time duration not greater than three hours.

4. Apparatus according to claim 1, with each predetermined insulin infusion profile having a limited time duration lying substantially within the range extending from one-half hour to three hours.

5. Apparatus according to claim 4, with said selection range of said input unit corresponding to a range of amounts of insulin extending from a low insulin amount to a high insulin amount many times greater than said low insulin amount.

6. Apparatus according to claim 1, with said selection range of said input unit corresponding to a range of amounts of insulin extending from a low insulin amount to a high insulin amount many times greater than said low insulin amount.

7. Apparatus according to claim 1, with said selection range of said input unit covering a multiplicity of different amounts of insulin.

8. Apparatus according to claim 1, with said selection range covering at least six different amounts of insulin.

9. Apparatus according to claim 1, with said control means controlling supply of a selectable basal rate of insulin in a range up to a given maximum basal delivery rate, and the input unit having a selection range corresponding to a number of different insulin amounts including at least five different amounts exceeding the amount supplied at the maximum basal delivery rate in a basal infusion time interval equal to said limited time duration.

10. An insulin infusion apparatus wherein diabetes therapy is under the manual control of the patient, without reliance on an implanted glucose sensor, said apparatus comprising a microdosing unit for dispensing said insulin into the patient, control means controlling said microdosing unit to supply a selected number of insulin units to the patient with an infusion profile as a function of time suitable for the patient after an individual meal, said control means having an input unit manually operable directly by the patient for entering, in accordance with the carbohydrate content of each individual meal, an input signal which selects a number representing the required number of insulin units to be delivered into the body of the patient, said control means being connected to be actuated by manual operation of said input unit by the patient to cause said microdosing unit to deliver the required number of insulin units according to the number selected by said input signal into the patient's body with said infusion profile as a funtion of time, said input unit having a selection range such that the number of insulin units is individually adaptable to each of the patient's meals by the operation of said input unit.

11. Apparatus according to claim 10, with said microdosing unit supplying a constant basal rate of insulin greater than zero during a basal infusion time interval.

12. Apparatus according to claim 11, with said infusion profile having a limited time duration not greater than three hours, and said basal infusion time interval being greater than said limited time duration.

13. Apparatus according to claim 10, with said infusion profile having a limited time duration lying substantially within a range extending from one-half hour to three hours.

14. Apparatus according to claim 13, with said selection range of said input unit corresponding to a range of amounts of insulin extending from a low number of insulin units to a high number of insulin units many times greater than said low number of insulin units.

15. Apparatus according to claim 10, with said selection range of said input unit corresponding to a range of amounts of insulin extending from a low number of insulin units to a high number of insulin units many times greater than said low number of insulin amount.

16. Apparatus according to claim 10, with said selection range of said input unit covering a multiplicity of different numbers of insulin units.

17. Apparatus according to claim 10, with said selection range covering at least six different numbers of insulin units.

18. Apparatus according to claim 10, with said control means controlling supply of a selectable basal rate of insulin in a range up to a given maximum basal delivery rate, and the input unit having a selection range corresponding to different numbers of insulin units including at least five different numbers of insulin units representing insulin delivery rates above said maximum basal delivery rate.

19. A glucose sensorless device for the preprogrammable infusion of insulin into a patient in diabetes therapy, comprising a microdosing unit for dispensing said insulin into the patient, control means including a program transmitter for transmitting a selected control program to said microdosing unit, said selected control program representing a selected infusion profile as a function of time, said control means having an input unit manually operable directly by the patient for entering, in accordance with the carbohydrate content absorbed by the patient at a meal, an input signal corresponding to a required number representing the insulin units to be delivered into the body of the patient, said control means being connected to be actuated by operation of said input unit by the patient to initiate via said program transmitter the infusion of said required number of insulin units, said microdosing unit thereby delivering said required number of insulin units into the patient's body with an infusion profile in conformity with said control program, said input unit providing for a selection range such that the number of insulin units is individually adaptable to each of the patient's meals by the operation of said input unit.

20. A glucose sensorless device according to claim 19, with said control means having storage means for storing at least one control program, said input unit being connected to said program transmitter to cause said program transmitter to transmit the selected control program via said storage means to said microdosing unit.

21. Apparatus for the pre-programmable infusion of liquids into a patient's body, comprising
a microdosing unit having supply means for supplying the liquid at a controllable infusion rate in response to programming signals,
control means operable for supplying selected programming signals to said microdosing unit for correspondingly controlling the rate of supply of the liquid thereby,
said control means having program storage means for storing at least one predeterminable control program, which provides for the generation of respective different programmed sequences of infusion amounts as a function of time, each of the respective different programmed sequences of infusion amounts as a function of time providing for the delivery of a respective different total liquid amount by said supply means over a time span suitable to an individual meal, with the different total liquid amounts lying within a predetermined available range of amounts suitable for selection by the patient,
said program storage means being controllable by each of a respective series of manually generated selection signals each representing a respective different one of said total liquid amounts to be infused within said available range of amounts and beginning at a given starting point, to generate the respective corresponding one of said programmed sequences of infusion amounts as a function of time over said time span and in accordance with said one control program stored therein, such that the respective corresponding total liquid amount is supplied by said microdosing unit in said time span,
said control means having manually actuatable input means coupled with said program storage means and being selectively manually actuable by the patient to respective positions corresponding to respective total liquid amounts within said available range of amounts to supply respective ones of said series of said manually generated selection signals and to supply the given starting time to the program storage means, whereby the microdosing unit is responsive to patient manual selection of one of said total liquid amounts from said available range of amounts and a desired starting point based on actual real time patient need while supplying such patient-selected total amount over a time span and at a rate as a function of time which is pre-programmed.

22. Apparatus according to claim 21, with the liquid supplied by said supply means being insulin.

23. Apparatus according to claim 22, with said manually actuatable input means having indicia means for providing a display in accordance with the amount of insulin to be supplied in each of the respective positions of said manually actuatable control means.

24. Apparatus according to claim 21, with the liquid supplied by said supply means being insulin, and said control means having constant rate transmitting means for controlling said microdosing unit to supply insulin at a constant base rate, the respective different programmed sequences of infusion amounts as a function of time provided for by said program storage means being superimposed on said constant base rate.

25. Apparatus according to claim 24, with said constant rate transmitter means having manually adjustable means accessible for manual actuation to effect adjustment of said constant base rate within a predetermined range.

26. Apparatus according to claim 21, with the liquid supplied by said supply means being insulin, and said control program stored by said program storage means representing a delivery profile specifically corresponding to the insulin requirements of the patient during digestion.

27. Apparatus according to claim 21, with said control program stored by said program storage means providing for the generation of essentially rectangular waveform programmed sequences as a function of time, said manually actuatable input means in its respective positions selecting respective different amplitudes for said essentially rectangular waveform programmed sequences.

28. Apparatus according to claim 21, with said control program stored by said program storage means providing for the generation of essentially rectangular waveform programmed sequences as a function of time, said manually actuatable input means in its respective positions selecting respective different time durations for said essentially rectangular waveform programmed sequences.

29. Apparatus according to claim 21, with said control program stored by said program storage means providing for the generation of essentially rectangular waveform programmed sequences as a function of time, said manually actuable control input means in its respective positions selecting respective different values of both amplitude and time duration for said essentially rectangular waveform programmed sequences.

30. Apparatus according to claim 21, with said control program stored by said program storage means providing for the generation of essentially triangular waveform programmed sequences as a function of time, said manually actuatable input means in its respective positions selecting respective different values of both peak amplitude and time duration for said essentially triangular waveform programmed sequences.

* * * * *